(12) United States Patent
Leibinger et al.

(10) Patent No.: US 11,096,728 B2
(45) Date of Patent: Aug. 24, 2021

(54) IMPLANT FOR OSTEOSYNTHESIS, AND IMPLANT KIT COMPRISING AN IMPLANT

(71) Applicant: Karl Leibinger Medizintechnik GmbH & Co. KG, Mühlheim (DE)

(72) Inventors: Christian Leibinger, Mühlheim (DE); Klaus Kohler, Mühlheim (DE)

(73) Assignee: Karl Leibinger Medizintechnik GmbH & Co. KG, Mühlheim (DE)

( * ) Notice: Subject to any disclaimer, the term of this patent is extended or adjusted under 35 U.S.C. 154(b) by 214 days.

(21) Appl. No.: 16/463,675

(22) PCT Filed: Dec. 11, 2017

(86) PCT No.: PCT/EP2017/082221
§ 371 (c)(1),
(2) Date: May 23, 2019

(87) PCT Pub. No.: WO2018/108812
PCT Pub. Date: Jun. 21, 2018

(65) Prior Publication Data
US 2021/0100595 A1      Apr. 8, 2021

(30) Foreign Application Priority Data

Dec. 15, 2016  (DE) .................. 10 2016 124 528.3

(51) Int. Cl.
*A61B 17/80*      (2006.01)
(52) U.S. Cl.
CPC ............................. *A61B 17/8057* (2013.01)

(58) Field of Classification Search
CPC . A61B 17/80; A61B 17/8052; A61B 17/8057; A61B 17/8061; A61B 17/8066;
(Continued)

(56) References Cited

U.S. PATENT DOCUMENTS 5,743,913 A * 4/1998 Wellisz .............. A61B 17/8061
                                                      606/285
6,123,709 A * 9/2000 Jones .................. A61B 17/1728
                                                      606/280

(Continued)

FOREIGN PATENT DOCUMENTS

DE            2410057 B1      7/1975
DE    102008002389 B4      5/2013
(Continued)

OTHER PUBLICATIONS

Jul. 6, 2017—German Search Report & English Translation.
(Continued)

*Primary Examiner* — Eric S Gibson
(74) *Attorney, Agent, or Firm* — Banner & Witcoff, Ltd.

(57) ABSTRACT

The invention relates to an implant (1) for osteosynthesis, comprising a securing region (3) that has a plurality of holes (2) for receiving securing means, and two projections (4) which extend away, at least partially curved, from said securing region (3), wherein at least one of the two projections (4) takes the form of a snap-on lug (5) that can snap onto a bone segment (7, 8) of a mammal bone (6); the invention also relates to an implant kit comprising such an implant (1).

20 Claims, 6 Drawing Sheets

(58) Field of Classification Search
CPC ............ A61B 17/8071; A61B 17/8076; A61B 17/8085

See application file for complete search history.

(56) References Cited

U.S. PATENT DOCUMENTS

| | | | |
|---|---|---|---|
| 8,821,552 B2 | 9/2014 | Reitzig et al. | |
| 8,900,281 B2 | 12/2014 | Reisberg | |
| 8,906,070 B2* | 12/2014 | Medoff | A61B 17/8004 606/280 |
| 8,940,019 B2 | 1/2015 | Gordon et al. | |
| 9,301,789 B2* | 4/2016 | Schonhardt | A61B 17/8085 |
| 10,080,599 B2* | 9/2018 | Caldarella | A61B 17/809 |
| 10,251,687 B2* | 4/2019 | Guo | A61B 17/8052 |
| 10,327,824 B2* | 6/2019 | Ricker | A61B 17/1767 |
| 10,849,664 B2* | 12/2020 | Caldarella | A61B 17/808 |
| 10,905,478 B2* | 2/2021 | Helfet | A61B 17/8085 |
| 2004/0210220 A1* | 10/2004 | Tornier | A61B 17/8061 606/284 |
| 2007/0043366 A1* | 2/2007 | Pfefferle | A61B 17/8061 606/279 |
| 2007/0123880 A1* | 5/2007 | Medoff | A61B 17/809 606/326 |
| 2007/0238069 A1* | 10/2007 | Lovald | A61B 17/8085 433/173 |
| 2009/0125069 A1* | 5/2009 | Sixto, Jr. | A61B 17/8047 606/286 |
| 2010/0198266 A1* | 8/2010 | Nassab | A61B 17/8085 606/280 |
| 2010/0217327 A1* | 8/2010 | Vancelette | A61B 17/8061 606/281 |
| 2011/0093018 A1 | 4/2011 | Prasad et al. | |
| 2011/0160730 A1* | 6/2011 | Schonhardt | A61B 17/085 606/71 |
| 2012/0203227 A1* | 8/2012 | Martin | A61B 17/8061 606/70 |
| 2012/0226279 A1* | 9/2012 | Lutz | A61B 17/8066 606/70 |
| 2013/0178905 A1* | 7/2013 | Graham | A61B 17/8085 606/282 |
| 2014/0128923 A1* | 5/2014 | Ellis | A61B 17/8076 606/286 |
| 2014/0172020 A1* | 6/2014 | Gonzalez-Hernandez | A61B 17/8061 606/281 |
| 2014/0194878 A1* | 7/2014 | Bernstein | A61B 17/8057 606/75 |
| 2014/0207197 A1* | 7/2014 | Reisberg | A61B 17/8863 606/324 |
| 2015/0327899 A1* | 11/2015 | Early | A61B 17/8085 606/280 |
| 2016/0367300 A1* | 12/2016 | Caldarella | A61B 17/808 |
| 2017/0065315 A1* | 3/2017 | Helfet | A61B 17/8061 |
| 2017/0105775 A1* | 4/2017 | Ricker | A61B 17/1767 |
| 2017/0319249 A1* | 11/2017 | Guo | A61B 17/8066 |
| 2018/0360509 A1* | 12/2018 | Caldarella | A61B 17/0644 |
| 2019/0262046 A1* | 8/2019 | Ricker | A61B 17/8061 |
| 2019/0380754 A1* | 12/2019 | Wiederkehr | A61B 17/8057 |

FOREIGN PATENT DOCUMENTS

| | | | |
|---|---|---|---|
| GB | 2435429 A | 8/2007 | |
| JP | 2020054828 A * | 4/2020 | ............ A61B 17/82 |
| RU | 2444322 C2 | 3/2012 | |
| WO | 2000062693 A1 | 10/2000 | |
| WO | 2015/131106 A1 | 9/2015 | |

OTHER PUBLICATIONS

Mar. 27, 2019—ISR & WO for PCT/EP2017/082221.
Feb. 16, 2021—(RU) Request for Substantive Examination—App 2019116445/14(031399)—Eng Tran.

* cited by examiner

IMPLANT FOR OSTEOSYNTHESIS, AND IMPLANT KIT COMPRISING AN IMPLANT

CROSS-REFERENCE TO RELATED APPLICATIONS

This application is a U.S. National Stage application under 35 U.S.C. § 371 of International Application PCT/EP2017/082221, filed Dec. 11, 2017, which claims the benefit of priority to Application DE 10 2016 124 528.3, filed Dec. 15, 2016. Benefit of the filing date of each of these prior applications is hereby claimed. Each of these prior applications is hereby incorporated by reference in its entirety.

The invention relates to an implant for osteosynthesis/for joining two bone segments of a separated/fractured mammal bone according to the preamble of claim 1, comprising a securing region that has a plurality of holes for receiving securing means and two projections which extend away, at least partially curved, from the securing region. At least one of the two projections being designed in the form of a snap-on lug which can be snapped onto a bone segment of a mammal bone. Thus, the implant is alternatively also referred to as osteosynthesis implant. Further, the invention relates to an implant kit comprising such an implant as well as a plurality of securing means according to claim 10.

Implants for osteosynthesis are already known from prior art. In this context, e.g. DE 10 2008 002 389 B4 discloses a device for osteosynthesis as well as for fixation and stabilization which is applied particularly to long bones. The device comprises a support web extending in a first longitudinal direction, at least one first clip laterally is extending from the support web and a second clip extending laterally from the support web, the second clip being arranged to be longitudinally offset relative to the first clip. The support web includes an area disposed between the first clip and the second clip which is formed to be bendable in two dimensions relative to the longitudinal axis of the support web. Further, the support web is formed integrally with the clips extending away from the support web. It is possible to rotate the first clip relative to the second clip about the longitudinal axis of the support web. In particular, said plastic deformation can be realized by three-point forceps. Further prior art is known from WO 2015/131106 A1.

Consequently, from prior art already implants including projections in the form of clips are known, wherein the clips are attached to a securing region to be plastically deformable.

However, it has turned out to be a drawback that handling of said implants, viz. especially attaching the implant to the separated bone areas, is relatively complicated. For this purpose, the intended shape of the implant has to be preset by means of a tool such as three-point forceps. That is, the implant has to be repeatedly applied to the bone segments to be joined after each bending operation so as to find out whether the properly bent implant including its clips also correctly encompasses and abuts on the respective bone segments. Unless this is the case, the implant has to be removed from the bone parts again and has to be properly re-bent. Thus, applying the implant to the respective bone segments is relatively complicated.

Therefore, it is the object of the present invention to eliminate said drawbacks known from prior art and, especially, to provide an implant which is to be adapted for the particular osteosynthesis application in as few working steps as possible. In particular, the expenditure for reworking the implant in the state of operation is intended to be largely avoided.

According to the invention, this object is achieved by the claimed subject matter of claim 1. That is, at least one of the two projections is elastically deformable relative to the securing region and in the secured state of the implant is positively connected to a bone segment. By snapping especially also a temporary elastic deformation of the snap-on lug is understood which entails only little deformation travel spring deflection. In particular, in this context also deformations are understood which cause a deformation travel spring deflection of the snap-on lug and/or of the entire implant of several $1/10$ mm. Hence, for example elastic deforming of the snap-on lug of about 0.1 mm is sufficient already to slide the implant over the corresponding bone segment and to make it snap onto the latter. Of particular advantage are deformation travels of less than 0.5 mm, alternatively also deformation paths of more than 0.5 mm can be realized, however. The securing region is reinforced, at least (annularly) around the holes for receiving securing means, as regards its thickness vis-à-vis the projections. Moreover, the securing region is lattice-shaped and a first web of the securing region includes a first group of holes for receiving securing means and a second web of the securing region tightly connected to the first web includes a second group of holes for receiving securing means.

This offers the technical advantage that in the area of the projections the implant no longer has to be intricately adapted to the three-dimensional contour of the fractured mammal bone. Due to their elastic nature, the projections automatically adapt to the respective area of the bone segment and tightly engage behind the respective bone segment in the secured state. For this purpose, during surgery the projections have to be attached to the bone segment while being slightly pretensioned. The naturally caused tolerances between bone segments of different individuals may be compensated by variable pretension. Additionally, the securing means can be tightened sufficiently strongly when securing the implant to the bone segments without inadvertently deforming the implant. The distribution of the holes for receiving securing means to webs renders the securing of the implant during surgery especially robust, on the one hand, and especially versatile, on the other hand.

Such configuration of the projections in the form of snap-on lugs is neither disclosed nor suggested in prior art, as in this case the respective projections are intended to be adapted even separately by plastic deformation to the individual areas of the mammal bone. The implant known from DE 10 2008 002 389 B4 used in the sternal area is intended to match the respective contour of the sternum and of the ribs by its plastic deformation at the support web and at the clips before it is finally joined to the bone segments.

Further advantageous embodiments are claimed in the subclaims and will be explained in detail hereinafter.

It is of particular advantage when the implant is used as a condylar implant, which is also referred to as condylar plate or condylar shoe. In this region it is especially complicated to adapt implants which have to be plastically deformed, and thus the implant according to the invention can be especially efficiently used.

It is further advantageous when the (two) projections are in the form of snap-on lugs and are arranged at the securing region so that they can be bent (away from each other) resiliently relative to each other. (Spring-type) resilient bending is understood to be temporary application of a bending force to the respective projection/the respective snap-on lug, the bending force being so low that the projection is not plastically deformed and subsequently will automatically return to its initial position. This helps to further facilitate attaching the implant to the fractured bone segment.

In total, the implant has especially such strength and shape that it is prepared/intended for abutting on the bone segments almost over a large part of the inner surface.

It is of further advantage when each of the projections has a thickness (material thickness/sheet thickness) ranging from 0.2 mm to 1.5 mm, preferably from 0.4 to 1.1 mm, further preferred from 0.45 mm to 0.8 mm, further preferred from 0.4 mm to 0.6 mm, especially preferred from 0.45 mm to 0.55 mm, even more preferred of 0.5 mm/0.5 mm. The implant thus is configured so that, on the one hand, it can be snapped onto the respective bone segment with sufficient strength and, on the other hand, the respective bone segment is not damaged by the projections being snapped on.

In order to prefix the implant particularly tightly by the projections, it is useful when the projections are curved and preferably extend away from the securing region by more than 90° along an imaginary curved line (extending in a plane or extending helically). In this way, it is realized that the bone segments are engaged from behind as far and tightly as possible in the inserted/attached state.

It is moreover advantageous when the implant (including the projections) is (completely) made from titanium material such as a titanium-aluminum alloy and, resp., a titanium-aluminum material, more preferred from Ti6Al4V (ASTM-F136). In this way, the implant can be manufactured at low cost by already well-proven materials. Alternatively, it is also advantageous, however, when the implant (including the projections) is made from plastic material such as polyetheretherketone (PEEK), with a fiber-reinforced plastic (including PEEK) being especially preferred. Basically, also other biocompatible materials such as other metals can be used, however.

It is of advantage in this context when the securing region is (at least partly) plate-shaped (i.e. extending in a plane) and/or (at least partly) shell-shaped (i.e. extending along a curved area). In this way, the respective bone segment can be encompassed in an especially robust manner.

In this context, it is further useful when the securing region, at least (annularly) around the holes for receiving securing means, has a thickness ranging from 0.6 mm to 2 mm, further preferred from 0.8 mm to 1.6 mm, more preferred from 0.9 mm to 1.1 mm, especially preferred of 1 mm/1 mm. The implant is thus formed to be especially stable but, on the other hand, not too thick to occupy too much space.

When at least one hole for receiving securing means is a slotted hole and/or at least one hole for receiving securing means is a (circular) threaded hole, the implant can be attached to the fractured mammal bone in an especially flexible and stable manner.

In this context, it is also useful when at least portions of the first web extend inclined relative to the second web. The first web extends e.g. along an imaginary curved or straight line of extension, whereas the second web extends along an imaginary curved or straight second line of extension. Then the holes for receiving securing means of the respective webs are stringed along said imaginary line of extension. This allows to fix the bone segments in a robust manner relative to each other.

It is further advantageous when at least one of the webs extends/is curved perpendicularly to its longitudinal extension. Thus, the implant can be adapted especially skillfully to the respective bone geometry.

Moreover, the invention relates to an implant kit comprising an implant according to one of the afore-described embodiments as well as comprising a plurality of securing means, preferably bone screws. In this way, also an implant kit is adapted to be attached in an especially stable and robust manner to the respective bone to be treated.

In this context, it is of further advantage when the securing means are at least partially in the form of screws having an outside diameter/outside thread diameter from 5 mm to 7 mm, especially preferred of about 6 mm, and thus in the form of screws of 5 mm to 7 mm, preferably 6 mm. Especially preferred are securing means having an outside diameter/outside thread diameter from 1.0 mm to 3.00 mm. In this way, the implant can be attached to the respective bone segment in an especially robust manner and can be used as condylar plate/shoe.

In the following, the invention will be illustrated in detail by way of figures, wherein various example embodiments are shown in this context.

The figures are merely schematic and exclusively serve for the comprehension of the invention. Like elements are provided with like reference numerals.

In FIGS. 1 to 6, initially a preferred first example embodiment of an implant 1 according to the invention is illustrated. As is clearly visible especially in FIG. 6, said implant 1 usually serves for osteosynthesis applications, i.e. for joining two previously separated/fragmented bone segments 7 and 8 of a mammal bone 6. The implant 1 is especially designed for use at a collum, a mandibular joint in this case, due to its shaping which will be described in detail below. In further configurations, it is also possible, however, to use said implant 1 in other regions of a skeleton of the mammal, such as at the fibula or at long bones such as the clavicle. The implant 1 is thus a condylar shoe in this example embodiment.

Figure 6:
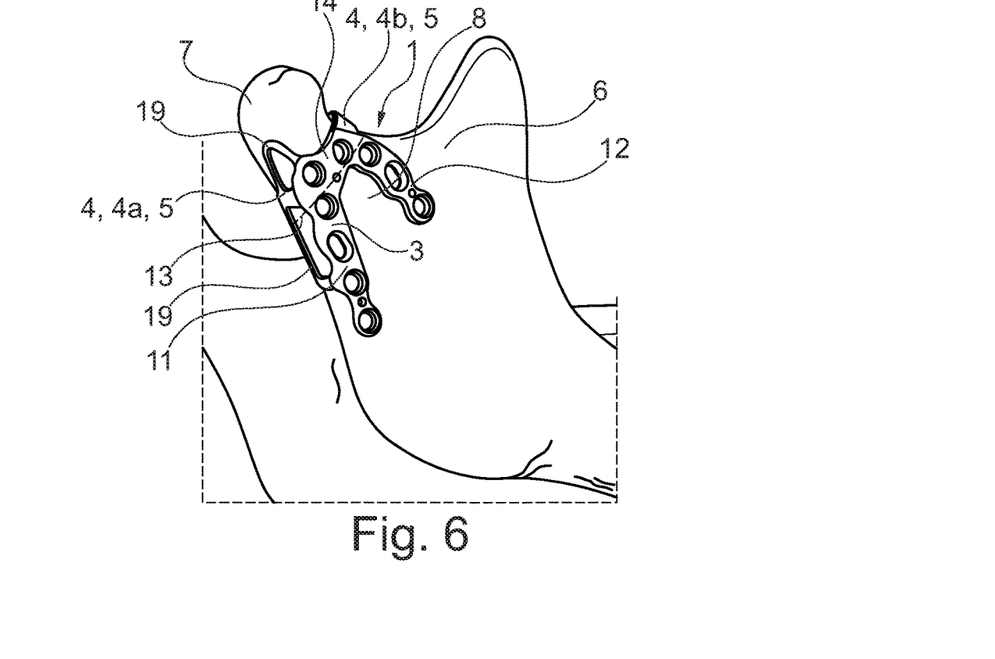
FIG. 6 shows a perspective view of the implant according to FIGS. 1 to 5 in a state attached to the mammal bone.

In FIG. 6, the implant 1 is already attached to the bone segments 7, 8 of the mammal bone 6, wherein a theoretical separating line 13 separating the two bone segments 7, 8 is marked by a broken line. The separating line 13 divides the mammal bone 6 into the first bone segment 7 and the second bone segment 8. The implant joins said two bone segments 7, 8 in the secured state by means of a plurality of securing means, viz. bone screws, not shown in detail here for the sake of clarity. The implant 1 is configured and adapted to the bone segments 7, 8 so that its inner surface facing the bone segments 7, 8 largely completely abuts on the bone segments 7, 8 in the attached state. It is outlined that also each of the implants 1 of the second to fourth example embodiments is configured and used similarly to the implant 1 of the first example embodiment; therefore, for the sake of clarity, hereinafter merely the substantial differences between the individual implants 1 will be described in detail.

Figure 1:
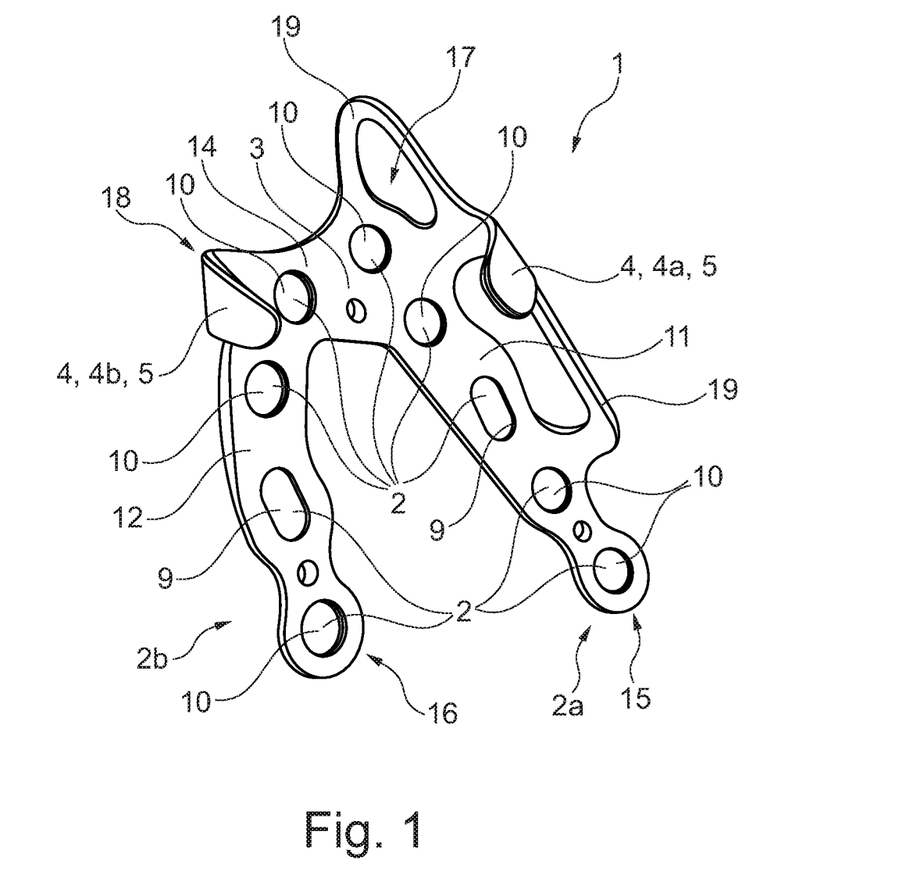
FIG. 1 shows a perspective view of an implant according to the invention as set forth in a first example embodiment, wherein especially the inside of the shell-type implant and the projections thereof are visible in their extension.

As is clearly evident from FIG. 1, the implant 1 has an overall shell-type design. The implant 1 includes a securing region 3. The securing region 3 is equally substantially shell-shaped/slightly bent in a lattice structure, as is also evident from FIG. 4. The securing region 3 has a plurality of holes 2 for receiving securing means into each of which a securing means in the form of a bone screw is introduced or can be introduced in the secured state. The holes 2 for receiving securing means are in the form of through-holes.

The securing region 6 includes a first web 11. The first web is especially clearly visible in its longitudinal extension from FIG. 2. The first web 11 has a constant (first) thickness. The first web 11 extends substantially along an imaginary first extension line which is straightly extending.

Moreover, the securing region 6 includes a second web 12. The second web 12 in turn has an elongate shape and extends slightly curved in its longitudinal direction, i.e. along an imaginary curved second extension line, as is clearly evident from FIG. 3. The second web 12 also has a constant thickness.

The two webs 11 and 12 of the securing region 6 are designed to be integrally, viz. made from one material, designed/connected to each other in a crown area 14. The two webs 11 and 12 extend substantially V-shaped/U-shaped so that a distance between their two imaginary lines of extension increases with an increasing distance from the crown area 14.

A first end 15 of the first web 11 in the form of a distal end protrudes from the crown area 14 in the same direction as a first end 16 of the second web 12 in the form of a distal end. At their two second ends 17 and 18 facing away from the respective first ends 15, 16 the two webs 11 and 12 are connected to each other and form the crown area 14. The webs 11 and 12 alternatively are also referred to as legs. The webs 11 and 12 are designed to have the same thickness.

As is again evident from FIG. 1, two projections 4 are connected to the securing region 3.

A first projection 4a abuts on the first web 11. Said first projection 4a is designed to be curved (FIG. 4) and extends from the first web 11 about more than 90°, viz. approx. about 140° to 170°, along a first imaginary curved line away from the securing region 3. The first curved line extends substantially in a plane.

Figure 2:
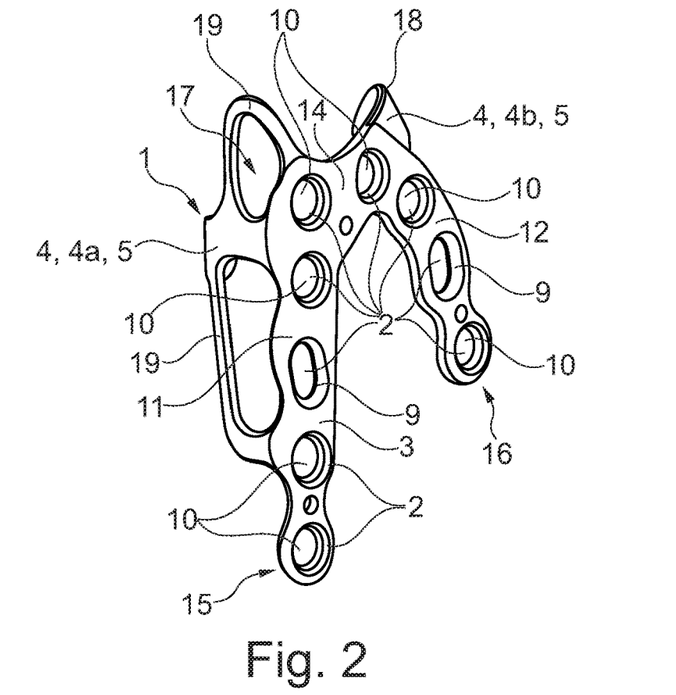
FIG. 2 shows a perspective view of the implant according to FIG. 1 from an outside which reveals a first web of a securing region and a thickening thereof around a plurality of holes for receiving securing means.
Figure 3:
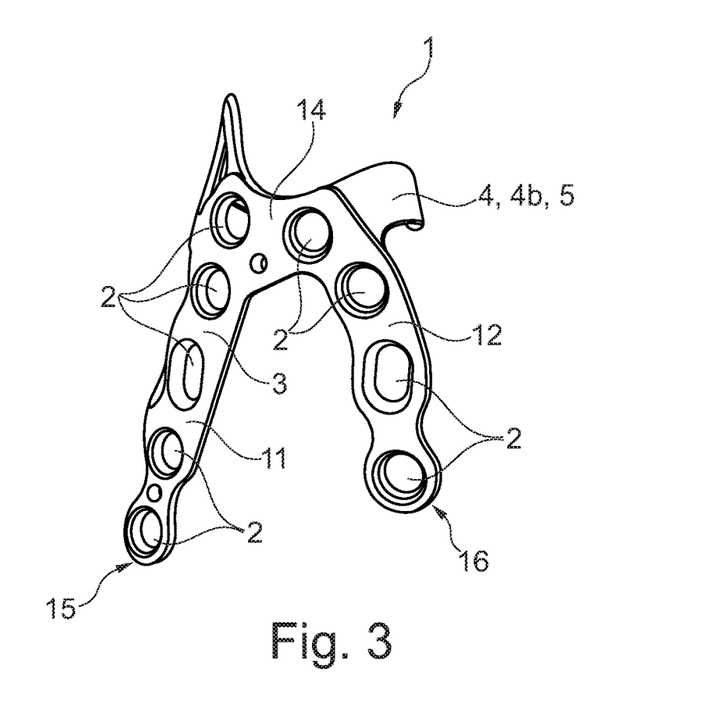
FIG. 3 shows a perspective view of the implant of FIGS. 1 and 2 from its outside, wherein the implant is shown to be rotated in space by approx. 90° vis-à-vis FIG. 2 so that especially a second web and the thickening thereof at the holes for receiving securing means is visible.
Figure 5:
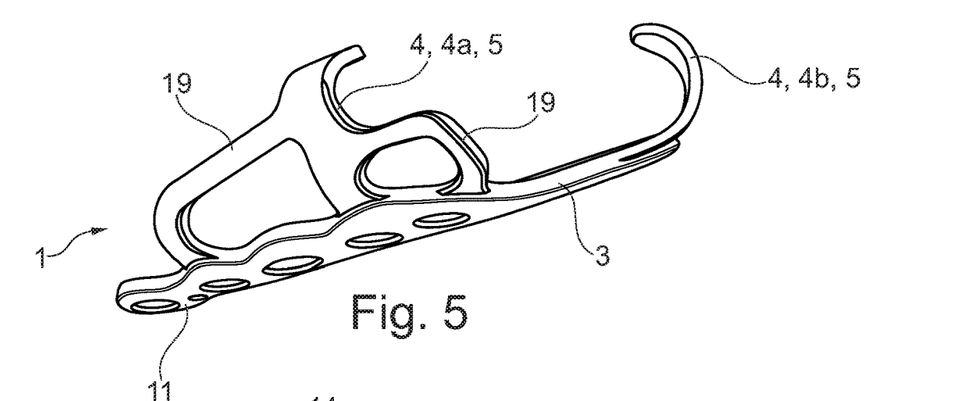
FIG. 5 shows a perspective view of the implant of FIGS. 1 to 4, wherein here a second projection is clearly visible in its extension.

The first projection 4a is additionally reinforced by means of support webs 19, as is clearly evident from a combination of the FIGS. 1, 2 and 5. Said support webs 19 are integrally attached by one end to the first projection 4a and by the other end to the securing region 3, i.e. to the first web 11.

A second projection 4b (FIG. 5) equally has a curved design. The second projection 4b extends away from the second web 12 in a curved manner. Said second projection 4b extends away from the first web 11 at an angle along an imaginary second curved line between 90° and 150°/170°. The second curved line extends substantially helically in space.

In total, the two projections 4a, 4b form a shell structure together with the securing region 3 and the support webs 19. Thus, the projections 4a, 4b serve as engaging elements which, in a state attached to the bone 6/the bone segments 7, 8, engage behind/encompass said bone 6/the respective bone segment 7, 8. The implant 1 as a whole is made from a material which is a biocompatible material in the form of metal, preferably a titanium material/a titanium alloy, further preferred a titanium-aluminum alloy such as Ti6Al4V.

According to the invention, the implant 1 is designed with its projections 4, 4a, 4b in the form of snap-on lugs 5. Both projections 4a and 4b thus are elastically deformable. As is visible in FIG. 6, the projections 4a and 4b are adjusted, as to their rough dimensions, to the geometry of the mammal bone 6 to be treated. During surgery the two projections 4a, 4b are snapped onto either of the two bone segments 7, 8, in this case the first bone segment 7. The projections 4a and 4b are elastically deformable to such extent that the implant 1 can be slid over/snapped onto the first bone segment 7 by the projections 4a and 4b.

The projections 4a and 4b are designed, as regards their thicknesses, to form the snap-on lugs 5. The projections 4a and 4b have a (second) thickness/material thickness of 0.5 mm. However, in further example embodiments also other thicknesses for the projections 4a and 4b can be realized, such as more than 0.5 mm, e.g. 0.8 mm or 1 mm. The (second) thickness of the projections 4a and 4b is always smaller than the (first) thickness of the securing region 3 and, resp., of the webs 11, 12. Therefore, the projections 4a, 4b are more elastic/more resilient than the securing region 3.

In order to maintain the preset geometry of the implant 1 in an as stable manner as possible when securing the implant, the thickness of the securing region 3, i.e. the webs 11, 12, around the holes 2 for receiving securing means is reinforced compared to that of the projections 4 and the support webs 19. The securing region 3/the two webs 11 and 12 have a (first) thickness of about 1 mm around the holes 2 for receiving securing means, i.e. in annular areas around the holes 2 for receiving securing means. The securing region 3 continuously has the same (first) thickness. However, in further example embodiments also other thicknesses can be selected for the securing region 3, such as e.g. a thickness ranging from 0.8 mm to 1.5 mm, wherein the (first) thickness of the webs 11, 12 is always larger than the (second) thickness of the projections 4a, 4b.

Moreover, each of the two webs 11 and 12 has a specific group 2a, 2b of holes 2 for receiving securing means. The first web 11 includes five holes 2 for receiving securing means which form a first group 2a. The second web 12 includes a second group 2b of holes 2 for receiving securing means comprising four holes 2 for receiving securing means. The groups 2a and 2b basically are not set at said number, however.

The holes 2 for receiving securing means are either in the form of a slotted hole 9, in the form of a threaded hole 10 or in the form of a threadless through-hole. The first web 11 includes, when viewed from the second end 17 to the first end 15, two threaded holes 10, one slotted hole 9 and again two threaded holes 10 in a stringed design. The second web 12 includes, when again viewed from the crown area 14, i.e. from the first end 16, to the second end 18, two threaded holes 10, one slotted hole 9 and one threaded hole 10 in a stringed design. The arrangement of said holes 2 for receiving securing means and the configurations thereof basically are not set at said order and design, however. It is also possible to arrange, instead of the slotted holes 9, alternatively a threaded hole 10 and, instead of the threaded holes 10, a slotted hole 9 or even to dispense with the configuration of slotted holes and threaded holes and to form them exclusively or partly as threadless through-holes, i.e. through-bores.

Figure 4:
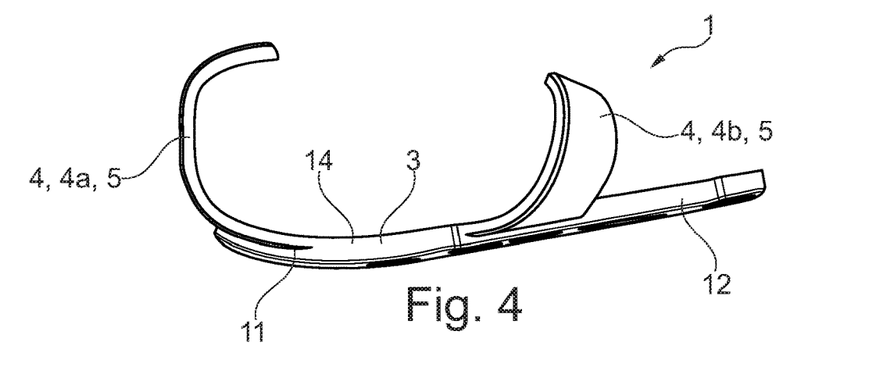
FIG. 4 shows a top view of the implant of FIGS. 1 to 3 so that a first projection of the implant is especially clearly visible in its curved extension.

The shell-type design of the implant 1 is also especially clearly visible in connection with FIGS. 4 to 6. The first web 11 is bent normal to its longitudinal extension. Although the first web 11 is slightly bent in this form, the area of the first and second webs 11 and 12 as well as the crown area are alternatively referred to/configured as a plate. In addition, the projections 4, 4a, 4b are alternatively referred to as clips/braces.

Figure 7:
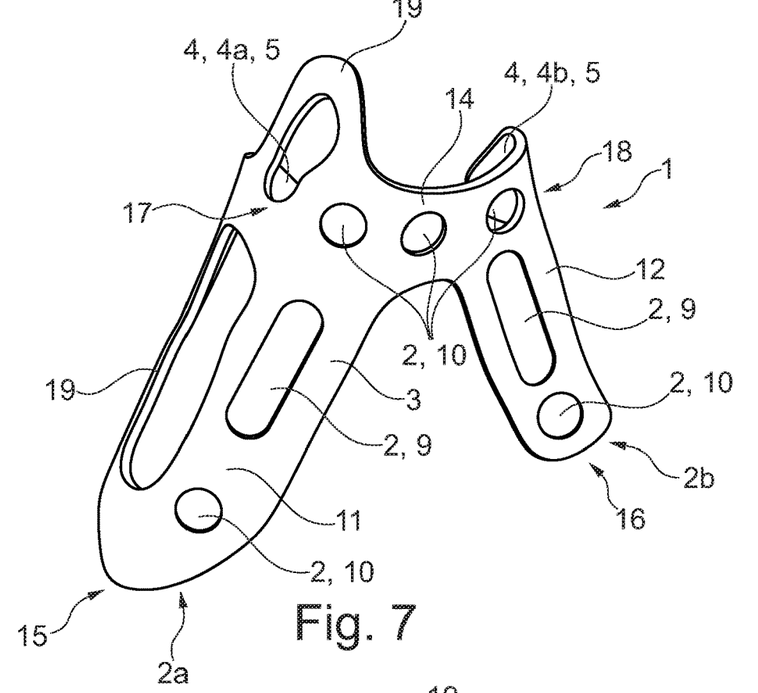
FIG. 7 shows a perspective view of an implant according to a second example embodiment, wherein the implant is shown from outside and, as compared to the implant of the first example embodiment, has a continuously uniform material thickness.
Figure 8:
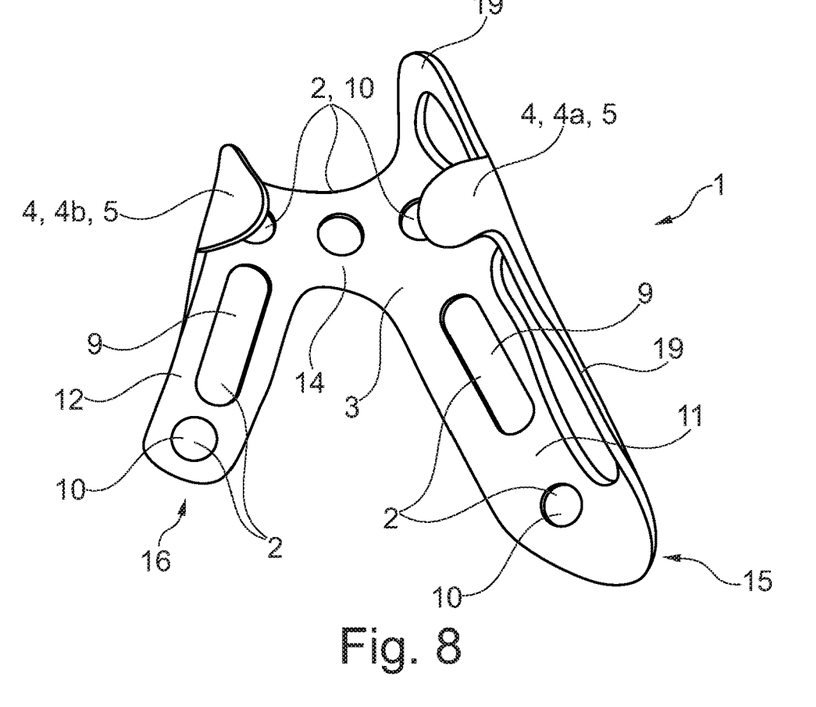
FIG. 8 shows a perspective view of the implant according to FIG. 7 from an inside so that again the projections are clearly visible.

According to the second example embodiment of FIGS. 7 and 8, it is also possible to produce the implant 1 to have a constant equal specific material thickness. It is especially preferred in this context when the material thickness of the entire implant 1, i.e. both in the securing region 3 having the webs 11 and 12 and at the projections 4, is 0.5 mm, in further configurations also 1 mm. In this case, in the crown area 14 an additional hole 2 for receiving securing means is introduced.

Figure 9:
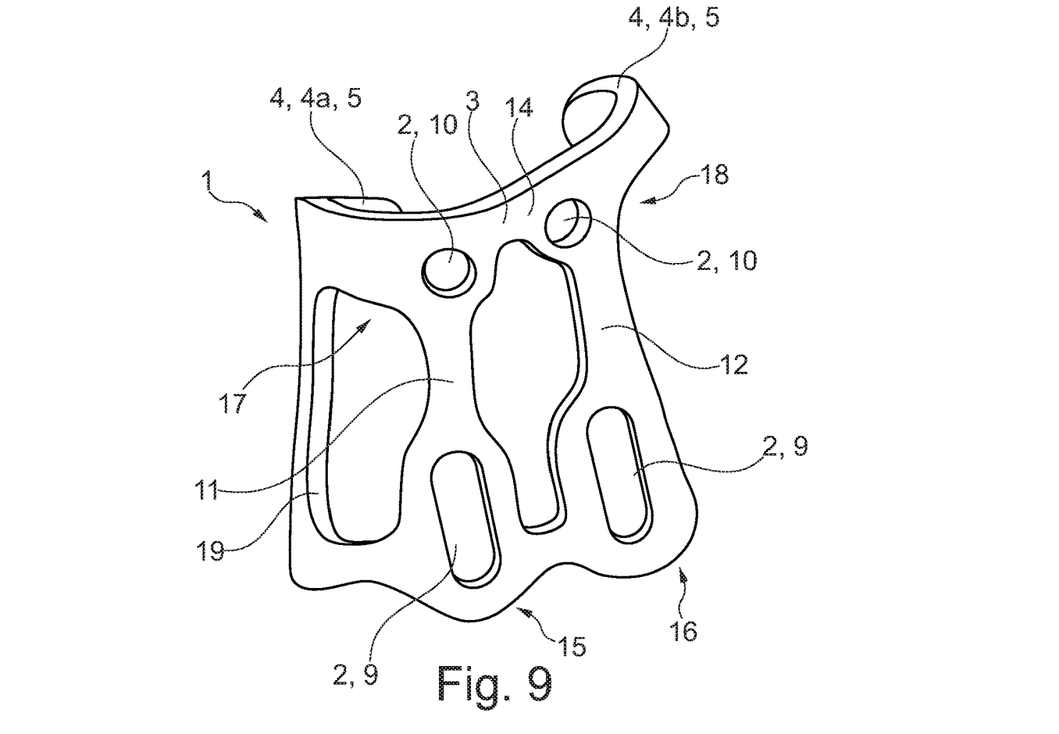
FIG. 9 shows a perspective view of an implant according to a third example embodiment from an outside, wherein the two webs of the securing region now are tightly joined at two ends.
Figure 10:
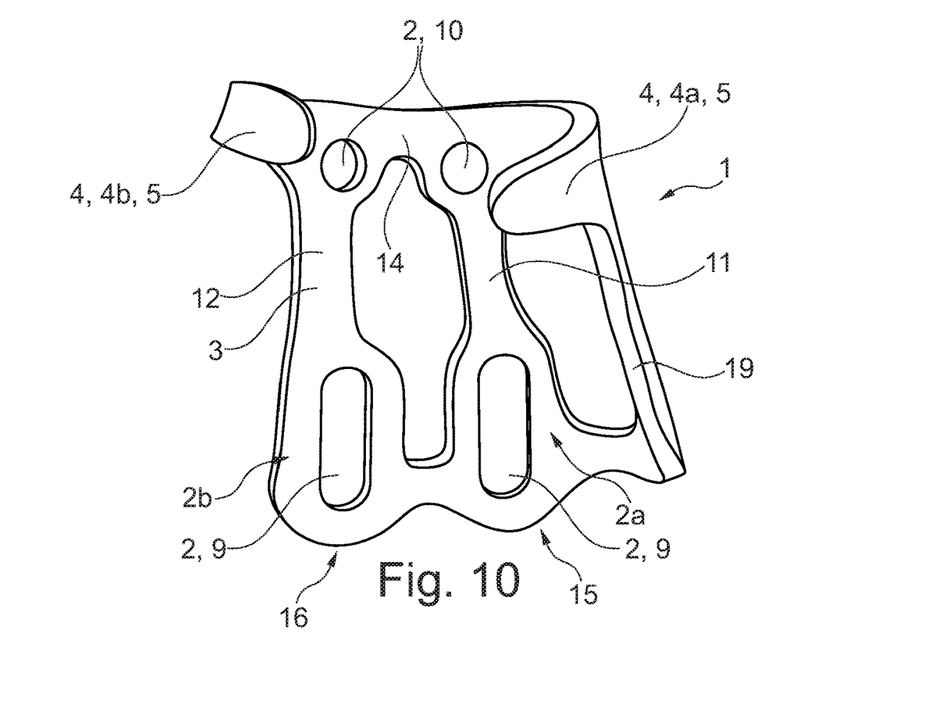
FIG. 10 shows a perspective view of the implant according to FIG. 9 from an inside, in which again the projections are clearly visible.

Also, in the further third example embodiment according to FIGS. 9 and 10 it is evident that the securing region 3 of the implant 1 is not set at a U-shaped/V-shaped lattice structure but may alternatively be in the form of a rectangular lattice structure. Thus, in this example embodiment, the two webs 11 and 12 are integrally connected to each other both at their first ends and at their second ends 15 to 18.

Figure 11:
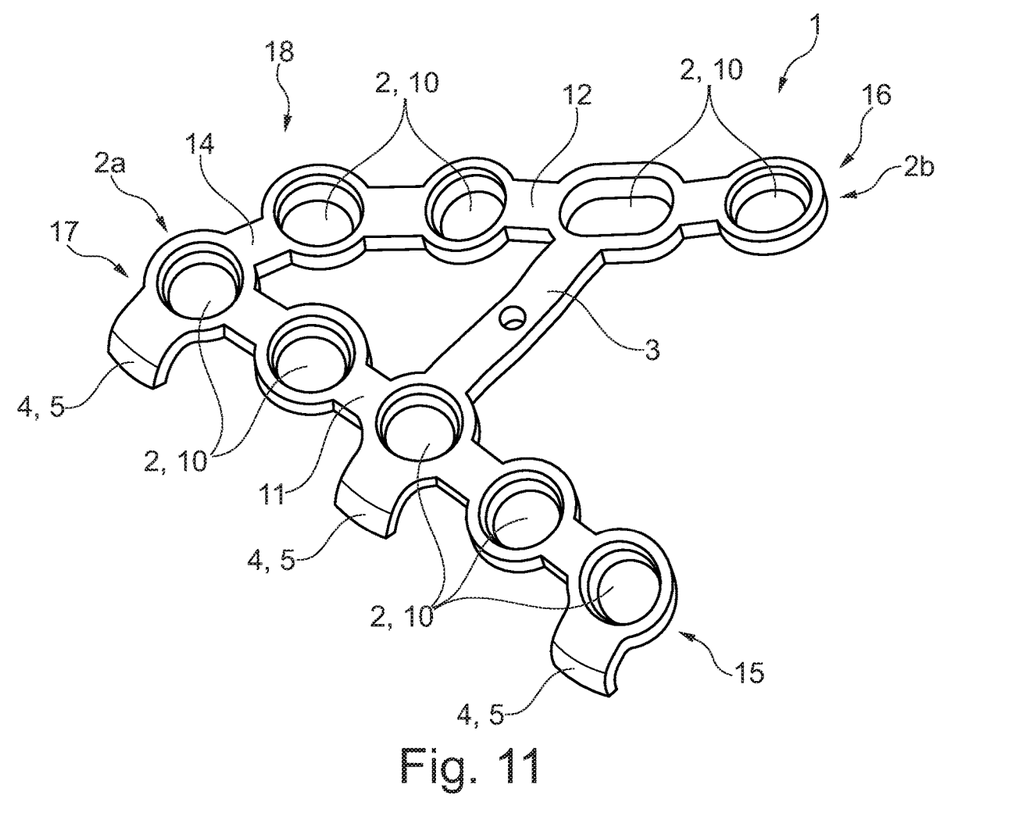
FIG. 11 shows a perspective view of an implant according to a fourth example embodiment from an outside, with projections being arranged at the first web only.

According to FIG. 11, it is also possible in accordance with a fourth example embodiment, to dispense with a projection at the second web and, as an alternative, to arrange plural projections 4, in this case three projections 4, at the first web 11. The projections 4 again extend directly away from the first web 11.

In other words, according to the invention, thus a plate (implant 1) is realized which can be inserted extremely easily and quickly. This is especially due to the cuff arms (projections 4), the flexible material/the flexible structure (preferably material thickness of 0.5 mm) and the supporting arms (webs 11, 12). Because of this, said plate 1 offers an obvious advantage over known designs. Because of this, said implant 1 is also preferably used as a condylar plate. As an alternative to this, it is also possible, however, to design the plate 1 in a different material thickness, such as in a material thickness of 1 mm.

The procedure during surgery is preferred in such way that initially an intraoral access to the collum is provided. After that, either the already separated mammal bone 6 and the bone segments 7 and 8 thereof are pre-aligned relative to each other into the correct position or, in the case of osteotomy of the collum, the mammal bone 6 is initially separated into the two bone segments 7 and 8 by the bone saw. After that, the fragment/bone segment 7 is laterally reduced by a tool, preferably a reduction hook. After that, the left cuff arm (first projection 4a) of the condylar plate 1 is hooked caudally beneath the fragment/bone segment 7. Then the plate 1 is pulled in the cranial direction so that also the right cuff arm (second projection 4b) clicks cranially. Subsequently, a first securing means, preferably a first screw, is set in the anterior side in the collar by a tool such as an Allen wrench. The second screw is equally inserted in the collar. The fracture is reduced and subsequently a third screw is loosely set in the center of a slotted hole 9, whereupon the plate 1 can still be corrected as to its position. After that, the screw is completely fixed in the slotted hole 9. Additional securing screws can further be introduced to the other holes for receiving inspection means, depending on the fracture line 13.

Thus, a condylar fragment can be seized and encompassed by a simple click principle. The two cuff arms 4a, 4b optimally encompass the fragment, thus enabling the operating principle of "fishing" the fragment to work equally in an optimum way. In this way, the fragment can be easily reduced. Especially a material thickness of the plate 1 of 0.5 mm, especially in the area of the projections 4a, 4b, is of advantage. Fixation is preferably carried out by 5 mm standard screws or 6 mm standard screws. Some of the screws may be introduced at a fixed angle. For this purpose, the plate 1 partially includes threaded bores/threaded holes 10 so that it is up to the user to attach the plate 1 using steel screws or angled screws.

Hence, also an implant kit, which is not shown here in detail for the sake of clarity, which comprises the implant 1 as well as a plurality of securing means in the form of screws, preferably standard screws, is formed.

LIST OF REFERENCE SIGNS 1 implant
2 hole for receiving securing means
2a first group of holes for receiving securing means
2b second group of holes for receiving securing means
3 securing region
4 projection
4a first projection
4b second projection
5 snap-on lug
6 mammal bone
7 first bone segment
8 second bone segment
9 slotted hole
10 threaded hole
11 first web
12 second web
13 separating line
14 crown area
15 first (distal) end of first web
16 first (distal) end of second web
17 second end of first web
18 second end of second web
19 support web

The invention claimed is:

1. An implant for osteosynthesis, comprising: a securing region including a plurality of holes for receiving securing means and first and second projections which extend away, at least partially curved, from the securing region, wherein at least one of the first and second projections takes the form of a snap-on lug that can snap onto a bone segment of a mammal bone, and the securing region is reinforced regarding its thickness, at least around the holes for receiving securing means, as compared to the first and second projections, wherein the securing region is lattice-shaped and a first web of the securing region includes a first group of holes for receiving securing means and the first projection and a second web of the securing region which is tightly connected to the first web includes a second group of holes for receiving securing means and the second projection, the implant further comprising at least one support web integrally attached at one end to the first projection and at the other end to the first web to align engagement of the implant on the bone.

2. The implant according to claim 1, wherein the first and second projections are in the form of respective snap-on lugs and are arranged at the securing region so that they are resiliently bendable relative to each other.

3. The implant according to claim 1, wherein each of the first and second projections has a thickness ranging from 0.2 mm to 1.5 mm.

4. The implant according to claim 1, wherein the first and second projections are formed in curved shape and extend away from the securing region by more than 90° along an imaginary curved line.

5. The implant according to claim 1, wherein the securing region is plate-shaped or shell-shaped.

6. The implant according to claim 1, wherein the securing region has a thickness ranging from 0.6 mm to 2 mm, at least around the holes for receiving securing means.

7. The implant according to claim 1, wherein at least one hole for receiving securing means is configured as a slotted hole and/or at least one hole for receiving securing means is configured as a threaded hole.

8. The implant according to claim 1, wherein at least portions of the first web extend inclined relative to the second web.

9. The implant according to claim 1, wherein at least one of the webs is curved perpendicularly to its longitudinal extension.

10. An implant kit comprising an implant claim 1 and comprising a plurality of securing means.

11. The implant kit according to claim 10, wherein the securing means are at least partly in the form of screws having a diameter ranging from 1.0 mm to 3.0 mm.

12. An implant comprising:
a securing region including a plurality of holes for receiving securing means; and
at least first and second projections which extend away, at least partially curved, from the securing region, wherein at least one of the at least first and second projections is configured to snap onto a bone,
wherein the securing region is lattice-shaped comprising a first web and a second web,
wherein the first web comprises a first group of holes for receiving securing means and the first projection,
wherein the second web, connected to the first web, comprises a second group of holes for receiving securing means and the second projection,
the implant further comprising at least one support web integrally attached at one end to the first projection and at the other end to the first web to align engagement of the implant on the bone.

13. The implant of claim 12, wherein at least a portion of the first web extends inclined relative to the second web.

14. The implant of claim 12, wherein the first web extends along an imaginary curved first line of extension.

15. The implant of claim 12, wherein the first web extends along an imaginary straight first line of extension.

16. The implant of claim 12, wherein the first web extends perpendicularly to its longitudinal extension.

17. The implant of claim 12, wherein the securing means are bone screws.

18. The implant of claim 12, wherein one of the first and second projections abuts the first web.

19. The implant of claim 12, wherein one of the first and second projections extends away from the first and second webs.

20. The implant of claim 12, wherein the first web is bent normal to its longitudinal extension.

* * * * *